United States Patent [19]

Choe et al.

[11] Patent Number: 4,983,325
[45] Date of Patent: * Jan. 8, 1991

[54] HIGH PERFORMANCE NONLINEAR OPTICAL MEDIA

[75] Inventors: Eui W. Choe, Randolph; Alan Buckley, Berkeley Height; Dagobert E. Stuetz, Watchung, all of N.J.; Anthony F. Garito, Radnor, Pa.

[73] Assignee: Hoechst Celanese Corp., Somerville, N.J.

[*] Notice: The portion of the term of this patent subsequent to Nov. 17, 2004 has been disclaimed.

[21] Appl. No.: 333,719

[22] Filed: Apr. 4, 1989

Related U.S. Application Data

[60] Division of Ser. No. 89,512, Aug. 26, 1987, abandoned, which is a continuation-in-part of Ser. No. 855,346, Apr. 24, 1986, abandoned, which is a division of Ser. No. 748,617, Jun. 25, 1985, Pat. No. 4,707,303.

[51] Int. Cl.$^5$ .................. G02B 5/172; G02F 1/00; H01S 3/10
[52] U.S. Cl. ........................ 252/600; 372/21; 307/425; 350/311; 350/353; 350/362; 252/582; 252/583; 252/587; 558/388
[58] Field of Search .................. 372/21; 307/425; 350/311, 353, 362; 252/583, 587, 582, 600; 558/388

[56] References Cited

U.S. PATENT DOCUMENTS

| | | | |
|---|---|---|---|
| 3,371,220 | 10/1966 | Fleury | 307/425 |
| 3,395,329 | 7/1968 | Rentzepis | 307/425 |
| 3,895,242 | 7/1975 | Yoshida | 307/425 |
| 3,965,375 | 6/1976 | Bergman, Jr. et al. | 307/88.5 |
| 4,199,698 | 4/1980 | Bethea | 307/425 |
| 4,376,899 | 3/1983 | Chemla | 307/425 |
| 4,428,873 | 1/1984 | Murayama et al. | 252/583 |
| 4,431,263 | 2/1984 | Garito | 350/96.34 |
| 4,624,872 | 11/1986 | Stuetz | 252/299.01 |

OTHER PUBLICATIONS

Garito, "Molecular Optics: Non-Linear Optical Processes", Mol. Cryst. Liq. Cryst., vol. 106, pp. 219-258, 1984.
Chemical & Engr. News, "Scientists Seek Nonlinear Optical Materials", Oct. 4, 1982, pp. 18-22.
Zyss, "New Organic Molecular Materials for Nonlinear Optics . . . ", J. Non-Cryst. Solids, 47.2, 1982, pp. 211-226.
Sigelle et al., "A New Material for Nonlinear Optics", J. Non-Cryst Solids, 47.2, 1982, 287-290.
Drabovich, et al., "Tunable Resonant", Optics Communications, vol. 20, No. 3, Mar. 1977, pp. 350-353.
Williams, "Organic Polymeric", Angew. Chem. Int. Ed. Engl. 23 (1984), 690-703.
Davydov, et al., "New Non-Linear", Sov. J. Quantum Electron., vol. 7, No. 1, Jan. 1977.
Tomaru, et al., "Second Harmonic Generation in Inclusion Complexes", J. Chem. Soc. Chem. Comm., No. 18, Sep. 15, 1984.
Jeunhomme, *Single Mode Fiber Optics*, Marcel Dekker Publ., pp. 257-268, 1983.

Primary Examiner—Mary C. Lee
Assistant Examiner—Catherine Scalzo
Attorney, Agent, or Firm—DePaoli & O'Brien

[57] ABSTRACT

In one embodiment this invention provides a high performance nonlinear optical medium which comprises a transparent organic polymer film containing an array of charge asymmetric molecules such as 13,13-diamino-14,14-dicyanodiphenoquinodimethane:

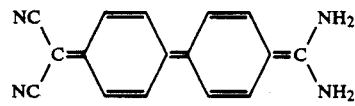

2 Claims, No Drawings

HIGH PERFORMANCE NONLINEAR OPTICAL MEDIA

This application is a division of application Ser. No. 089,512, filed Aug. 26, 1987, now abandoned, which is a continuation-in-part of patent application Ser. No. 855,346 filed Apr. 24, 1986, now abandoned, which is a divisional filing of patent application Ser. No. 748,617, filed Jun. 25, 1985, now U.S. Pat. No. 4,707,303.

BACKGROUND OF THE INVENTION

Nonlinear optics deals with the interaction of light waves due to an electromagnetic field dependent susceptibility of an optically transparent substrate. Nonlinear optical effects are observed at light intensities which are sufficiently high that the electric field of the light waves is significant in comparison with the Coulomb electric field binding the electrons in the atoms and molecules of the light transmitting solid medium. Monochromatic light of the required intensity (e.g., $10^7$ V/cm) first became available with the discovery of the laser in 1960.

It is known that organic and polymeric materials with large delocalized $\pi$-electron systems can exhibit nonlinear optical response, which in many cases is a much larger response than that shown by inorganic media.

In addition, the properties of organic and polymeric materials can be varied to optimize other desirable properties, such as mechanical and thermoxidative stability and high laser damage threshold, with preservation of the electronic interactions responsible for nonlinear optical effects.

Thin films of organic or polymeric materials with large second order nonlinearities in combination with silicon-based electronic circuitry have potential as systems for laser modulation and deflection, information control in optical circuitry, and the like.

Other novel processes occurring through third order nonlinearity such as degenerate four-wave mixing, whereby real-time processing of optical fields occurs, have potential utility in such diverse fields as optical communications and integrated circuit fabrication.

Of particular importance for conjugated organic systems is the fact that the origin of the nonlinear effects is the polarization of the $\pi$-electron cloud as opposed to displacement or rearrangement of nuclear coordinates found in inorganic materials.

Nonlinear optical properties of organic and polymeric materials was the subject of a symposium sponsored by the ACS division of Polymer Chemistry at the 18th meeting of the American Chemical Society, September 1982. Papers presented at the meeting are published in ACS Symposium Series 233, American Chemical Society, Washington, D.C. 1983.

The above recited publications are incorporated herein by reference.

There is continuing research effort to develop new nonlinear optical organic systems for prospective novel phenomena and devices adapted for laser frequency conversion, information control in optical circuitry, light valves and optical switches. The potential utility of organic materials with large second-order and third-order nonlinearities for very high frequency application contrasts with the bandwidth limitations of conventional inorganic electrooptic materials.

Accordingly, it is an object of this invention to provide novel high performance nonlinear optical media.

It is another object of this invention to provide nonlinear optical organic media exhibiting a high $\chi^{(2)}$ susceptibility value.

It is another object of this invention to provide a solid phase nonlinear optical organic medium characterized by a high Miller's delta, an absence of interfering fluorescence, and a high optical damage threshold.

It is a further object of this invention to provide a nonlinear optical medium which comprises a noncentrosymmetric configuration of aligned molecules having a diphenoquinodimethane conjugated structure.

Other objects and advantages of the present invention shall become apparent from the accompanying description and examples.

DESCRIPTION OF THE INVENTION

One or more objects of the present invention are accomplished by the provision of a nonlinear optical organic medium exhibiting a $\chi^{(2)}$ susceptibility of at least about $1 \times 10^{-7}$ esu.

In another embodiment this invention provides a nonlinear optical organic medium exhibiting a $\chi^{(2)}$ susceptibility of at least about $1 \times 10^{-7}$ esu, and an absence of interfering fluorescence in the wavelength range between about 0.3–3 $\mu$m.

In another embodiment this invention provides a nonlinear optical organic medium exhibiting a $\chi^{(2)}$ susceptibility of at least about $1 \times 10^{-7}$ esu, an absence of interfering fluorescence in the wavelength range between about 0.3–3 $\mu$m, and an optical loss less than about 1.0 decibel per centimeter.

In another embodiment this invention provides a nonlinear optical organic medium exhibiting a $\chi^{(2)}$ susceptibility of at least about $1 \times 10^{-7}$ esu, an absence of interfering fluorescence in the wavelength range between about 0.3–3 $\mu$m, an optical loss less than about 1.0 decibel per centimeter, and a response time less than about $10^{-13}$ second.

In another embodiment the invention provides a nonlinear optical organic medium exhibiting a $\chi^{(2)}$ susceptibility of at least about $1 \times 10^{-7}$ esu, an absence of interfering fluorescence in the wavelength range between about 0.3–3 $\mu$m, an optical loss less than about 1.0 decibel per centimeter, a response time less than about $10^{-13}$ second, and phase matching of fundamental and second harmonic frequencies.

In another embodiment the invention provides a nonlinear optical organic medium exhibiting a $\chi^{(2)}$ susceptibility of at least about $1 \times 10^{-7}$ esu, an absence of interfering fluorescence in the wavelength range between about 0.3–3 $\mu$m, an optical loss less than about 1.0 decibel per centimeter, a response time less than about $10^{-13}$ second, phase matching of fundamental and second harmonic frequencies, and a dielectric constant less than about 5.

In another embodiment this invention provides an optically transparent medium comprising a noncentrosymmetric or centrosymmetric array of molecules having a charge asymmetric diphenoquinodimethane conjugated structure.

The term "charge asymmetric" as employed herein refers to the dipolarity characteristic of organic molecules containing an electron-withdrawing group which is in conjugation with an electron-donating group.

In another embodiment this invention provides a nonlinear optical organic medium exhibiting a $\chi^{(2)}$ susceptibility of at least about $1 \times 10^{-7}$ esu, an absence of interfering fluorescence in the wavelength range between about 0.3-3 μm, an optical loss less than about 1.0 decibel per centimeter, a response time less than about $10^{-13}$ second, phase matching of fundamental and second harmonic frequencies, a dielectric constant less than about 5, and wherein the medium comprises a noncentrosymmetric configuration of aligned molecules having a charge asymmetric diphenoquinodimethane conjugated structure.

In another embodiment this invention provides a nonlinear optical organic medium exhibiting a $\chi^{(2)}$ susceptibility of at least about $1 \times 10^{-7}$ esu, an absence of interfering fluorescence in the wavelength range between about 0.3-3 μm, an optical loss less than about 1.0 decibel per centimeter, a response time less than about $10^{-13}$ second, phase matching of fundamental and second harmonic frequencies, a dielectric constant less than about 5, and wherein the medium comprises a noncentrosymmetric configuration of aligned molecules having a diphenoquinodimethane conjugated structure corresponding to the formula:

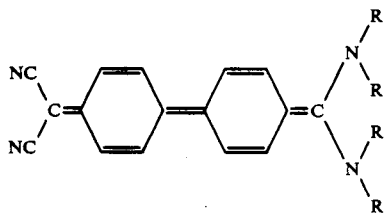

where R is a substituent selected from hydrogen and alkyl groups.

In another embodiment this invention provides a nonlinear optical organic medium exhibiting a $\chi^{(2)}$ susceptibility of at least about $1 \times 10^{-7}$ esu, an absence of interfering fluorescence in the wavelength range between about 0.3-3 μm, an optical loss less than about 1.0 decibel per centimeter, a response time less than about $10^{-13}$ second, phase matching of fundamental and second harmonic frequencies, a dielectric constant less than about 5, and wherein the medium comprises a noncentrosymmetric configuration of aligned molecules having a diphenoquinodimethane conjugated structure corresponding to the formula:

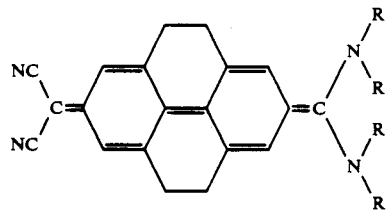

where R is a substituent selected from hydrogen and alkyl groups.

The diphenoquinodimethane molecules can have an external field-induced uniaxial molecular orientation in a host liquid medium, or an external field-induced stable uniaxial molecular orientation in a host solid medium.

In another embodiment this invention provides a nonlinear optical organic medium exhibiting a Miller's delta of at least about 3 square meters/coulomb.

In another embodiment this invention provides a solid phase nonlinear optical organic medium characterized by a Miller's delta of at least about 3 square meters/coulomb, a vapor pressure less than about $10^{-6}$ torr, and an optical damage threshold of at least about one gigawatt per square centimeter.

This invention further contemplates the provision of an optically transparent medium comprising a noncentrosymmetric or centrosymmetric configuration of a 13,13-diamino-14,14-dicyanodiphenoquinodimethane type or a 13,13-diamino-14,14-dicyano-4,5,9,10-tetrahydropyrenoquinodimethane type of molecules, wherein the amino groups can be either substituted or unsubstituted.

In a further embodiment this invention provides a nonlinear optical medium comprising a solid polymeric medium having incorporated therein a distribution of 13,13-diamino-14,14-dicyanodiphenoquinodimethane or 13,13-diamino-14,14-dicyano-4,5,9,10-tetrahydropyrenoquinodimethane molecules, wherein the amino groups can be either substituted or unsubstituted.

The term "Miller's delta" as employed herein with respect to second harmonic generation (SHG) is defined by Garito et al in Chapter 1, "Molecular Optics:-Nonlinear Optical Properties Of Organic And Polymeric Crystals"; ACS Symposium Series 233 (1983).

The quantity "delta"(δ) is defined by the equation:

$$d_{ijk} = \epsilon_o \chi_{ii}^{(1)} \chi_{jj}^{(1)} \chi_{kk}^{(1)} \delta_{ijk}$$

where terms such as $\chi_{ii}^{(1)}$ are the linear susceptibility components, and $d_{ijk}$, the second harmonic coefficient, is defined through $$\chi_{ijk}^{(2)}(-2\omega; \omega,\omega) = 2\ d_{ijk}(-2\omega; \omega,\omega)$$

The Miller's delta ($10^{-2}$ m²/c at 1.06 μm) of various nonlinear optical crystalline media are illustrated by KDP (3.5), LiNbO₃(7.5), GaAs(1.8) and 2-methyl-4-nitroaniline (160).

Such comparative FIGURES of merit are defined over the frequency range extending to zero frequency, or equivalently DC, and the polarization electrooptic coefficient as described in the publication by Garito et al recited above.

The term "fluorescence" as employed herein refers to an optical effect in which a molecule is excited by short wavelength light and emits light radiation at a longer wavelength. The fluorescence effect is described with respect to liquid dye lasers in "Optoelectronics, An Introduction", pages 233-236, Prentice Hall International, Englewood Cliffs, N.J.(1983).

The term "optical loss" as employed herein is defined by the equation:

$$\alpha L = 10 \log (I_o/I)$$

where
  α = attenuation coefficient ratio of lost light per unit length
  L = sample length
  $I_o$ = intensity of incident light
  I = intensity of transmitted light.

The term "optical scattering loss" is defined and measured quantitatively by $$T_\perp / T_\parallel$$

where $T_\perp$ is the transmission of optical radiation through the test sample between polarizers perpendicular to each other, and $T_{\parallel}$ is the transmission between polarizers parallel to each other.

The term "response time" as employed herein refers to numerous physical mechanisms for nonlinear optical responses and properties of nonlinear optical materials. The fastest intrinsic response time to light radiation is a physical mechanism based on electronic excitations characterized by a response time of about $10^{-14}$–$10^{-15}$ seconds. Response time is a term descriptive of the time associated with optical radiation causing promotion of an electron from the electronic ground state to an electronic excited state and subsequent de-excitation to the electronic ground state upon removal of the optical radiation.

The term "phase matching" as employed herein refers to an effect in a nonlinear optical medium in which a harmonic wave is propagated with the same effective refractive index as the incident fundamental light wave. Efficient second harmonic generation requires a nonlinear optical medium to possess propagation directions in which optical medium birefringence cancels the natural dispersion, i.e., the optical transmission of fundamental and second harmonic frequencies is phase matched in the medium. The phase matching can provide a high conversion percentage of the incident light to the second harmonic wave.

For the general case of parametric wave mixing, the phase matching condition is expressed by the relationship:

$$n_1\omega_1 + n_2\omega_2 = n_3\omega_3$$

where $n_1$ and $n_2$ are the indexes of refraction for the incident fundamental radiation, $n_3$ is the index of refraction for the created radiation, $\omega_1$ and $\omega_2$ are the frequencies of the incident fundamental radiation and $\omega_3$ is the frequency of the created radiation. More particularly, for second harmonic generation, wherein $\omega_1$ and $\omega_2$ are the same frequency $\omega$, and $\omega_3$ is the created second harmonic frequency, $2\omega$, the phase matching condition is expressed by the relationship:

$$n_\omega = n_{2\omega}$$

where $n_\omega$ and $n_{2\omega}$ are indexes of refraction for the incident fundamental and created second harmonic light waves, respectively. More detailed theoretical aspects are described in "Quantum Electronics" by A. Yariv, chapters 16–17 (Wiley and Sons, New York, 1975).

The term "dielectric constant" as employed herein is defined in terms of capacitance by the equation:

$$\epsilon = \frac{C}{C_o}$$

where
C = capacitance when filled with a material of dielectric constant $\epsilon$
$C_o$ = capacitance of the same electrical condenser filled with air.

The term "external field" as employed herein refers to an electric, or magnetic or mechanical stress field which is applied to a medium of mobile organic molecules, to induce dipolar alignment of the molecules parallel to the field.

The term "optically transparent" as employed herein refers to an optical medium which is transparent or light transmitting with respect to incident fundamental light frequencies and created light frequencies. In a nonlinear optical device, a present invention nonlinear optical medium is transparent to both the incident and exit light frequencies.

NONLINEAR OPTICAL PROPERTIES

The fundamental concepts of nonlinear optics and their relationship to chemical structures can be expressed in terms of dipolar approximation with respect to the polarization induced in an atom or molecule by an external field.

As summarized in the ACS Symposium Series 233(1983), the fundamental equation (1) below describes the change in dipole moment between the ground state $\mu_g$ and an excited state $\mu_e$ expressed as a power series of the electric field E which occurs upon interaction of such a field, as in the electric component of electromagnetic radiation, with a single molecule. The coefficient $\alpha$ is the familiar linear polarizability, $\beta$ and $\gamma$ are the quadratic and cubic hyperpolarizabilities, respectively. The coefficients for these hyperpolarizabilities are tensor quantities and therefore highly symmetry dependent. Odd order coefficients are nonvanishing for all structures on the molecular and unit cell level. The even order coefficients such as $\beta$ are non-zero for those structures lacking a center of inversion symmetry on the molecular and unit cell level.

Equation (2) is identical with (1) except that it describes a macroscopic polarization, such as that arising from an array of molecules in a crystal.

$$\mu\Delta = \mu_e - \mu_g = \alpha E + \beta EE + \gamma EEE + \quad (1)$$

$$P = P_0 + \chi^{(1)}E + \chi^{(2)}EE + \chi^{(3)}EEE + \quad (2)$$

Light waves passing through an array of molecules can interact with them to produce new waves. This interaction may be interpreted as resulting from a modulation in refractive index or alternatively as a nonlinearity of the polarization. Such interaction occurs most efficiently when certain phase matching conditions are met, requiring identical propagation speeds of the fundamental wave and the harmonic wave. Birefringent crystals often possess propagation directions in which the refractive index for the fundamental $\omega$ and the second harmonic $2\omega$ are identical so that dispersion may be overcome.

A present invention organic medium typically is optically transparent and exhibits hyperpolarization tensor properties such as second harmonic and third harmonic generation, and the linear electrooptic (Pockels) effect. For second harmonic generation, the bulk phase of the organic medium whether liquid or solid does not possess a real or orientational average inversion center. The medium is a macroscopic noncentrosymmetric structure.

Harmonic generation measurements relative to quartz can be performed to establish the value of second-order and third order nonlinear susceptibility of the optically clear media.

In the case of macroscopic nonlinear optical media that are composed of noncentrosymmetric sites on the molecular and unit cell level, the macroscopic second order nonlinear optical response $\chi^{(2)}$ is comprised of the corresponding molecular nonlinear optical response $\beta$. In the rigid lattice gas approximation, the macroscopic susceptibility $\chi^{(2)}$ is expressed by the following relationship:

$$\chi_{ijk}(-\omega_3;\omega_1,\omega_2) = Nf^{\omega_3}f^{\omega_2}f^{\omega_1}<\beta_{ijk}(-\omega_3;\omega_1,\omega_2)>$$

wherein N is the number of sites per unit volume, f represent small local field correlations, $\beta_{ijk}$ is averaged over the unit cell, $\omega_3$ is the frequency of the created optical wave, and $\omega_1$ and $\omega_2$ are the frequencies of the incident fundamental optical waves.

These theoretical considerations are elaborated by Garito et al in chapter 1 of the ACS Symposium Series 233 (1983) recited hereinabove; and by Lipscomb et al in J. Chem. Phys., 75, 1509 (1981), incorporated by reference. See also Lalama et al, Phys. Rev., A20, 1179 (1979); and Garito et al, Mol. Cryst. and Liq. Cryst., 106, 219 (1984); incorporated by reference.

FIELD-INDUCED MICROSCOPIC NONLINEARITY

The microscopic response, or electronic susceptibility $\beta$, and its frequency dependence or dispersion, is experimentally determined by electric field induced second harmonic generation (DCSHG) measurements of liquid solutions or gases as described in "Dispersion Of The Nonlinear Second Order Optical Susceptibility Of Organic Systems", Physical Review B, 28 (No. 12), 6766 (1983) by Garito et al, and the Molecular Crystals and Liquid Crystals publication cited above.

In the measurements, the created frequency $\omega_3$ is the second-harmonic frequency designated by $2\omega$, and the fundamental frequencies $\omega_1$ and $\omega_2$ are the same frequency designated by $\omega$. An applied DC field removes the natural center of inversion symmetry of the solution, and the second harmonic signal is measured using the wedge Maker fringe method. The measured polarization at the second harmonic frequency $2\omega$ yields the effective second harmonic susceptibility of the liquid solution and thus the microscopic susceptibility $\beta$ for the molecule.

For purposes of the present invention, a class of organic compounds which exhibit extremely large values of $\beta$ is one containing a noncentrosymmetric diphenoquinodimethane structure. Illustrative of this class of compounds is 13,13-diamino-14,14-dicyanodiphenoquinodimethane (DCNDQA):

The DCNDQA molecule is characterized by a single excited state at 2.2 eV(0.6); a dipole moment difference of $\Delta\mu_1^x$:23D; a transition moment of $\mu^x_{1g}$:13.6D; and large $2\omega$ and $\omega$ contributions to $\beta$ of order $10^3$ at $1\mu$–$0.6\mu$, and no interfering $2\omega$ resonance from higher excitations.

SOLID ORGANIC GUEST-HOST MEDIA

In one of its embodiments this invention provides nonlinear optically transparent polymeric media having incorporated therein a distribution of dipolar diphenoquinodimethane guest molecules.

Illustrative of this type of optical medium is a methyl methacrylate film containing a distribution of DCNDQA molecules.

If the distribution of guest molecules is random, there is orientational averaging by statistical alignment of the dipolar molecules in the polymeric host, and the optical medium exhibits third order nonlinearity ($\chi^{(3)}$).

If the distribution of guest molecules is at least partially uniaxial in molecular orientation, then the optical medium exhibits second order nonlinearity ($\chi^{(2)}$). One method for preparing polymeric films with large second-order nonlinear coefficients is to remove the orientational averaging of a dopant molecule with large $\beta$ by application of an external DC electric field or magnetic field to a softened film. This can be accomplished by heating the film above the host polymer glass-transition temperature $T_g$, then cooling the film below $T_g$ in the presence of the external field. The poling provides the alignment predicted by the Boltmann distribution law.

The formation of a thin host polymer medium containing guest molecules having, for example, uniaxial orthogonal molecular orientation can be achieved by inducing a dipolar alignment of the guest molecules in the medium with an externally applied field of the type described above.

In one method a thin film of the polymer (e.g., methyl methacrylate) containing guest molecules (e.g., DCNDQA) is cast between electrode plates. The polymer medium then is heated to a temperature above the second order transition temperature of the polymer. A DC electric field is applied (e.g., at a field strength between about 400–100,000 V/cm) for a period sufficient to align all of the guest molecules in a unidirectional orthogonal configuration parallel to the transverse field. Typically the orientation period will be in the range between about one second and one hour, as determined by factors such as guest molecular structure and field strength.

When the orientation of guest molecules is complete, the polymer medium is cooled below its second order transition temperature, while the medium is still under the influence of the applied DC electric field. In this manner the uniaxial orthogonal molecular orientation of guest molecules is immobilized in a rigid structure.

The uniaxial molecular orientation of the guest molecules in the polymer medium can be confirmed by X-ray diffraction analysis. Another method of molecular orientation measurement is by optical characterization, such as optical absorption measurements by means of a spectrophotometer with a linear polarization fixture.

QUINODIMETHANE COMPOUNDS

Another aspect of the present invention is the utilization of a quinodimethane compound as a charge asymmetric component of nonlinear optical media.

The quinodimethane structures of particular interest are those corresponding to the formulae:

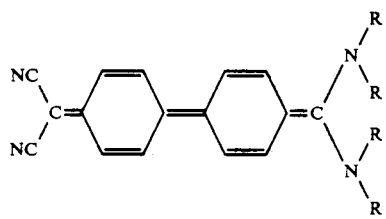

-continued

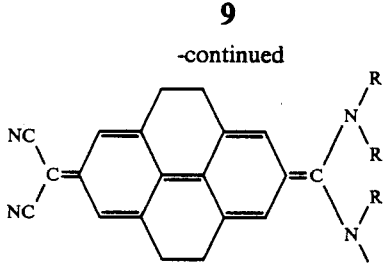

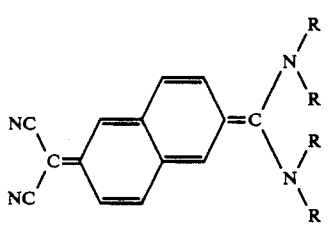

where R is hydrogen or an alkyl group. Illustrative of alkyl groups are methyl, ethyl, propyl, isopropyl, butyl, isobutyl, pentyl, decyl, hexadecyl, eicosyl, and the like. Alkyl groups containing between about 1–20 carbon atoms are preferred. The $NR_2$ group can also represent a heterocyclic group such as piperidyl, piperizyl or morpholinyl.

The $=C(NR_2)_2$ moiety in the formulae can constitute a heterocyclic radical in which the two amino groups taken together with the connecting methylidene carbon atom form a cyclic structure such as imidazole in the quinodimethane compounds:

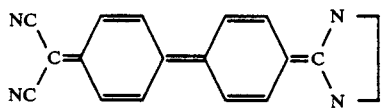

The quinodimethane compounds can also contain substituents which have one or more optically active asymmetric centers, such as chiral isomeric structures corresponding to the formulae:

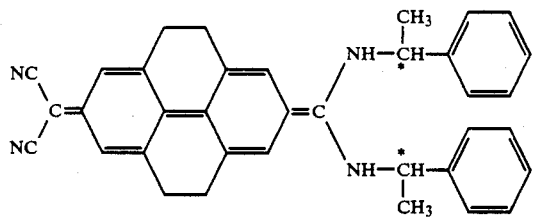

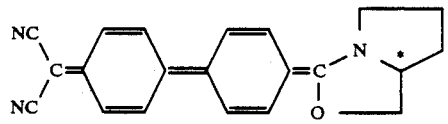

In the above-illustrated structural formulae, the cyclic groups can have one or more of the hydrogen positions on the ring carbon atoms replaced with a substituent such as alkyl, halo, alkoxy, phenyl, and the like, or can be integrated as part of a more complex fused polycyclic ring structure.

The quinodimethane compounds are more fully described in U.S. Pat. No. 4,640,800; and copending patent application Ser. No. 864,203, filed May 19, 1986.

The following examples are further illustrative of the present invention. The components and specific ingredients are presented as being typical, and various modifications can be derived in view of the foregoing disclosure within the scope of the invention.

Fluorescence activity in a nonlinear optical medium is measured by Perkin-Elmer Fluorescence Spectroscopy Model No. MPF-66 or LS-5.

Optical loss exhibited by a nonlinear optical medium is measured by optical time domain reflectometry or optical frequency-domain reflectometry as described in "Single-mode Fiber Optics" by Luc B. Jeunhomme, Marcel Dekker Inc., New York, 1984. It is also measured by the method described in "The Optical Industry And Systems Purchasing Directory", Photonics, 1984. The optical scattering loss is quantitatively measured by the ratio of perpendicular transmission to parallel transmission of a He-Ne laser beam through the nonlinear sample which is placed between crossed polarizers.

The response time of a nonlinear optical medium is calculated by the method described in "Optoelectronics; An Introduction" by P. J. Deau, Editor, Prentice-Hall International.

The dielectric constant of a nonlinear optical medium is measured by the methods described in Chapter XXXVIII of "Technique of Organic Chemistry", Volume I, Part III, (Physical Methods of Organic Chemistry) by Arnold Weissberger, Editor, Interscience Publishers Ltd., New York, 1960.

EXAMPLE I

This Example illustrates the preparation of 13,13-diamino-14,14-dicyano-4,5,9,10-tetrapyrenoquinodimethane in accordance with the present invention.

Ten grams of 13,13,14,14-tetracyano-4,5,9,10-tetrahydropyrenoquinodimethane prepared by the synthetic scheme previously described and 2 liters of tetrahydrofuran are placed in a three-necked three-liter flask equipped with a mechanical stirrer, a nitrogen inlet, a drying tube and a gas-inlet connected to an anhydrous ammonia gas tank. Ammonia gas is bubbled through the stirred solution for three days at room temperature. The crude product in precipitate form is filtered from the reaction mixture, washed with distilled water, and recrystallized from DMF-water to yield high purity 13,13-diamino-14,14-dicyano-4,5,9,10-tetrahydropyrenoquinodimethane product. DC induced second harmonic generation can achieve a second order nonlinear optical susceptibility $\chi^{(2)}$ of about $1.5\times10^{-7}$ esu, and a Miller's delta of about 4 square meters/coulomb in the product.

When a NLO medium of the product is centrosymmetric in macroscopic configuration, it can exhibit a nonlinear optical susceptibility $\chi^{(3)}$ of about $2.5\times10^{-9}$ esu, a response time of less than $10^{-13}$ second, an absence of fluorescence in the wavelength range between about 0.3–3 $\mu$m, an optical loss less than about 1.0 decibel per centimeter, and a dielectric constant less than about 5.

EXAMPLE II

This Example illustrates the preparation of 13,13-di(n-hexydecylamino)-14,14-dicyano-4,5,9,10-tetrahydropyrenoquinodimethane in accordance with the present invention.

A three-necked three-liter flask equipped with a mechanical stirrer, a nitrogen inlet, a drying tube, and an addition funnel is charged with 10 grams (0.03 moles) of 13,13,14,14-tetracyano-4,5,9,10-tetrahydropyrenoquinodimethane and two liters of tetrahydrofuran. Twenty-nine grams (0.12 moles) of n-hexadecylamine in 100 ml of tetrahydrofuran is added dropwise into the flask, and the resulting mixture is stirred for three days at room temperature. The resulting THF solution is concentrated on a rotary evaporator.

The crude product in precipitate form is separated by filtration, washed with distilled water, neutralized with 10% solution of ammonium hydroxide, washed with water, and then recrystallized from N,N-dimethylformamide-water to yield 13,13-di(n-hexadecylamino)-14,14-dicyano-4,5,9,10-tetrahydropyrenoquinodimethane. This compound is aligned in a melt-phase in a DC field by applying about 15K volts/cm, and cooled slowly to freeze the aligned molecular structure in the DC field. The aligned molecular medium is optically transparent and can exhibit a second order nonlinear optical susceptibility $\chi^{(2)}$ of about $1.5 \times 10^{-7}$ esu, and a Miller's delta of about 4 square meters/coulomb.

In a medium in which the molecules are randomly distributed, the product can exhibit a third order nonlinear optical susceptibility $\chi^{(3)}$ of about $2.5 \times 10^{-9}$ esu. The other properties are similar to those described for the Example I product.

EXAMPLE III

This Example illustrates the preparation of 13,13-diamino-14,14-dicyanodiphenoquinodimethane in accordance with the present invention.

Following the procedure of Example I, 13,13-diamino-14,14-dicyanodiphenoquinodimethane is prepared by ammonia treating a tetrahydrofuran solution containing 10 grams of 13,13,14,14-tetracyanodiphenoquinodimethane that is obtained by the synthesis scheme previously described.

DC induced second harmonic generation can provide a second order nonlinear optical susceptibility $\chi^{(2)}$ of about $1 \times 10^{-7}$ esu in the product.

In a product medium with a centrosymmetric molecular configuration, the susceptibility $\chi^{(3)}$ can be about $2 \times 10^{-9}$ esu. The other medium properties are similar to those described for the Example I product.

EXAMPLE IV

This Example illustrates the preparation of 13,13-di(n-hexyldecylamino)-14,14-dicyanodiphenoquinodimethane.

Following the procedure of Example II, 13,13-di(n-hexadecylamino)-14,14-dicyanodiphenoquinodimethane is prepared by employing a tetrahydrofuran solution containing ten grams of 13,13,14,14-tetracyanodiphenoquinodimethane and thirty-two grams of n-hexadecylamine. The second order nonlinear optical susceptibility $\chi^{(3)}$ can be about $1 \times 10^{-7}$ esu after alignment of molecules in a DC field, or after alignment of molecules by the Langmuir-Blodgett Technique in which a monolayer or several layers of molecules are deposited on a glass substrate.

EXAMPLE V

This Example illustrates the use of 13,13-di(n-hexyldecylamino)-14,14-dicyano-4,5,9,10-tetrahydropyrenoquinodimethane as a guest molecule in a polymer medium.

Ten grams of 13,13-di(n-hexadecylamino)-14,14-dicyano-4,5,9,10-tetrahydropyrenoquinodimethane and 90 grams of poly(methyl methacrylate) are dissolved in 400 ml of methylene chloride. A film (2 mil) is cast from this solution on a glass plate coated with indium tin oxide. Another glass plate coated with indium tin oxide is placed on the film, and then the film is heated to about 150° C. A DC field is applied to align the molecules, and the film is cooled slowly in the applied field to yield an aligned polymer alloy which can have a second order nonlinear susceptibility $\chi^{(2)}$ of about $1 \times 10^{-7}$ esu.

What is claimed is:

1. A transparent nonlinear optical medium produced by a process which comprises subjecting a melt-phase organic medium characterized by an optical susceptibility $\chi^{(3)}$ of at least about $2 \times 10^{-9}$ esu to an external field to induce a noncentrosymmetric molecular orientation of mobile molecules, wherein the induced molecular orientation is maintained when the melt-phase is solidified, and wherein the transparent nonlinear optical organic substrate is characterized by an optical susceptibility $\chi^{(2)}$ of at least about $1 \times 10^{-7}$ esu, an absence of interfering fluorescence in the wavelength range between about 0.3–3 $\mu$m, and an optical loss less than about 1.0 decibel per centimeter.

2. A transparent nonlinear optical medium produced by a process which comprises subjecting a melt-phase organic medium characterized by an optical susceptibility $\chi^{(3)}$ of at least about $2 \times 10^{-9}$ esu to an external field to induce a noncentrosymmetric molecular orientation of mobile molecules, wherein the induced molecular orientation is maintained when the melt-phase is solidified, and wherein the transparent nonlinear optical organic substrate is characterized by an optical susceptibility $\chi^{(2)}$ of at least about $1 \times 10^{-7}$ esu, an absence of interfering fluorescence in the wavelength range between about 0.3–3 $\mu$m, an optical loss less than about 1.0 decibel per centimeter, a response time less than about $10^{-13}$ second, and phase matching of fundamental and second harmonic frequencies.

* * * * *